(12) United States Patent
Bader

(10) Patent No.: US 11,925,602 B2
(45) Date of Patent: Mar. 12, 2024

(54) PACIFIER

(71) Applicant: Monika Bader, Cologne (DE)

(72) Inventor: Monika Bader, Cologne (DE)

( * ) Notice: Subject to any disclaimer, the term of this patent is extended or adjusted under 35 U.S.C. 154(b) by 78 days.

(21) Appl. No.: 17/397,228

(22) Filed: Aug. 9, 2021

(65) Prior Publication Data

US 2022/0040047 A1 Feb. 10, 2022

(30) Foreign Application Priority Data

Aug. 10, 2020 (DE) ...................... 20 2020 104 607.1

(51) Int. Cl.
*A61J 17/00* (2006.01)
*A61B 5/00* (2006.01)
*A61B 5/03* (2006.01)

(52) U.S. Cl.
CPC ........... *A61J 17/001* (2015.05); *A61B 5/0004* (2013.01); *A61B 5/038* (2013.01); *A61J 17/101* (2020.05); *A61J 17/103* (2020.05); *A61B 2503/04* (2013.01); *A61B 2560/04* (2013.01); *A61B 2562/0247* (2013.01); *A61B 2562/0271* (2013.01); *A61J 2200/72* (2013.01)

(58) Field of Classification Search
CPC ........... A61J 17/00–113; A61J 2200/72; A61J 2017/002; A61J 2017/006; A61B 5/0004; A61B 5/0038; A61B 2503/04; A61B 2560/04; A61B 2562/0247; A61B 2562/0271
See application file for complete search history.

(56) References Cited

U.S. PATENT DOCUMENTS

| | | | | |
|---|---|---|---|---|
| 5,033,864 A | * | 7/1991 | Lasecki | G01K 3/005 374/E1.004 |
| 5,551,952 A | * | 9/1996 | Falgout | A61J 17/101 601/139 |
| 5,693,073 A | * | 12/1997 | Glick | A61J 17/101 606/236 |
| 5,902,322 A | * | 5/1999 | Scagliotti | A61J 17/02 606/235 |
| 6,702,765 B2 | * | 3/2004 | Robbins | A61B 5/682 600/590 |
| 10,008,080 B1 | * | 6/2018 | Cooper | G08B 21/24 |
| 2001/0047189 A1 | * | 11/2001 | Griffith | A61J 17/105 606/234 |
| 2004/0093033 A1 | * | 5/2004 | Desousa | A61J 17/101 606/235 |
| 2005/0251211 A1 | * | 11/2005 | Knifong | A61J 17/101 606/234 |
| 2008/0140119 A1 | * | 6/2008 | Machtiger | A61B 5/01 606/234 |
| 2009/0069848 A1 | * | 3/2009 | Marcus | A61J 17/02 606/235 |
| 2009/0156967 A1 | * | 6/2009 | Cohen | A61B 5/1107 73/865.4 |

(Continued)

FOREIGN PATENT DOCUMENTS

| | | |
|---|---|---|
| AT | 521733 A1 | 4/2020 |
| DE | 20303360 U1 | 4/2003 |

(Continued)

*Primary Examiner* — Vi X Nguyen
(74) *Attorney, Agent, or Firm* — Dilworth & Barrese, LLP

(57) ABSTRACT

Suggested is a pacifier, comprising a mouthpiece and a shield further including a vibration-generating device.

12 Claims, 2 Drawing Sheets

(56) References Cited

U.S. PATENT DOCUMENTS

| | | | |
|---|---|---|---|
| 2009/0198275 A1* | 8/2009 | Godown | A61J 17/103 |
| | | | 606/236 |
| 2012/0078143 A1* | 3/2012 | Hernandez | A61H 21/00 |
| | | | 606/236 |
| 2013/0245687 A1* | 9/2013 | Bachmann | A61J 17/02 |
| | | | 606/235 |
| 2015/0272447 A1* | 10/2015 | Ford | A61J 17/107 |
| | | | 600/549 |
| 2017/0095406 A1* | 4/2017 | Hakim | A61J 17/113 |
| 2020/0138673 A1* | 5/2020 | Vargo | A61H 23/02 |
| 2021/0177706 A1* | 6/2021 | Ferrill | A61J 17/1012 |

FOREIGN PATENT DOCUMENTS

| | | |
|---|---|---|
| DE | 202008000122 U1 | 4/2008 |
| DE | 202019000832 U1 | 3/2019 |

\* cited by examiner

PACIFIER

FIELD OF THE INVENTION

The invention is in the field of infant products and relates to a particular pacifier.

TECHNOLOGICAL BACKGROUND

Pacifiers (dummies) serve to satisfy the need to suck infants and toddlers have. Modern dummies in their present form were introduced in the USA by C. W. Meinecke around the year 1900, and substantially consist of a mouthpiece which is made of latex or silicone, and a shield which prevents any swallowing of the mouthpiece. Two shapes of the mouthpiece (teat) may be distinguished: the round cherry shape, and the orthodontic shape which is flattened at the front and is thus adapted to the shape of the palate in the oral cavity. The orthodontic shape was developed by the dentist Adolf Müller in 1949.

RELEVANT STATE OF THE ART

Pacifiers having additional functionalities are known in the state of the art. DE 10 2015 011030 A1 (SCHEIB) relates to a pacifier which is equipped with a combined moisture and temperature sensor which may broadcast possible warning signals through embedded electronics in the shield by short-range radio communication or mobile communications.

DE 20 2017 06939 U1 (KOCHER) claims a dummy which is connected to a device which releases active substances in the form of aerosols when activated by the sucking reflex.

DE 20 2019 000832 U1 (ZEYEN) describes a dummy which may be retrievable through acoustic signals. It comprises a teat, a shield having electronics installed therein for the receipt of radio signals and for the reproduction of sound signals, and a separate wireless remote control consisting of a housing having electronics installed therein for emitting radio signals.

AT 521733 A (HOFFMANN) describes a teat which analyses the behaviour of the infant by monitoring both their sucking and the movement of the dummy, and which prevents the infant from suffering sudden infant death syndrome by emitting haptic or acoustic stimuli. In addition, the teat wirelessly transmits notifications about the behaviour of the infant to a smartphone.

PROBLEM TO BE SOLVED

Therefore, the problem of the present invention was to provide a pacifier, which is also referred to as dummy, which has an improved soothing effect when compared to conventional, commercially available products.

DESCRIPTION OF THE INVENTION

In a first embodiment, the invention relates to a pacifier, comprising a mouthpiece and a shield, which is characterised in that it further includes a vibration-generating device.

Surprisingly, it was found that a gentle vibration of the pacifier, which is activated by pressure applied to the teat, may lead to a significantly faster soothing of the infant or the toddler.

BRIEF DESCRIPTION OF THE DRAWINGS

The present invention will be described in greater detail with reference to the accompanying drawings, in which.

DESCRIPTION OF THE PREFERRED EMBODIMENTS

Teat

Figure 1:
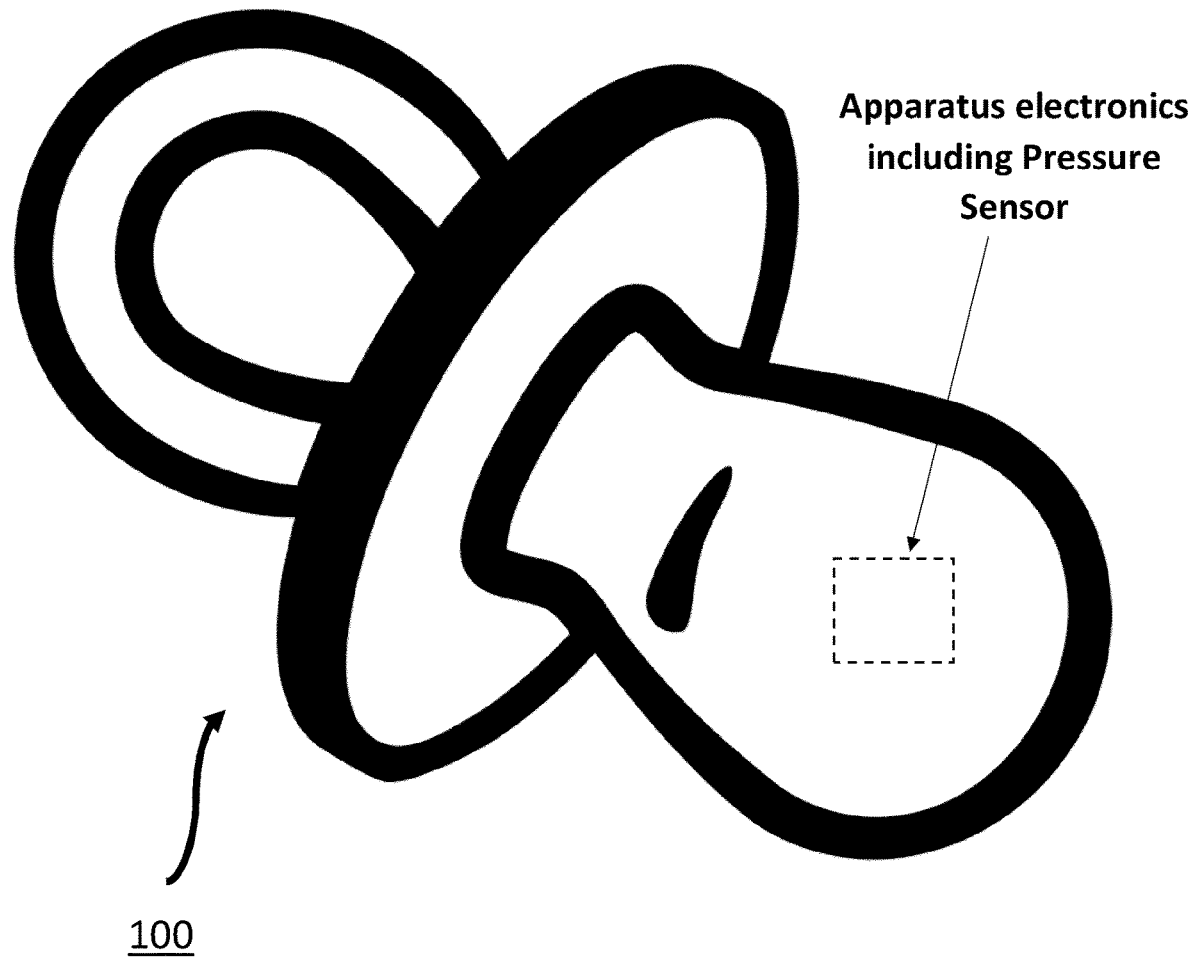
FIG. 1 is a perspective view of a pacifier in accordance with the present invention, and FIG. 2 schematically illustrates components forming part of the pacifier in accordance with the present invention.
Figure 2:
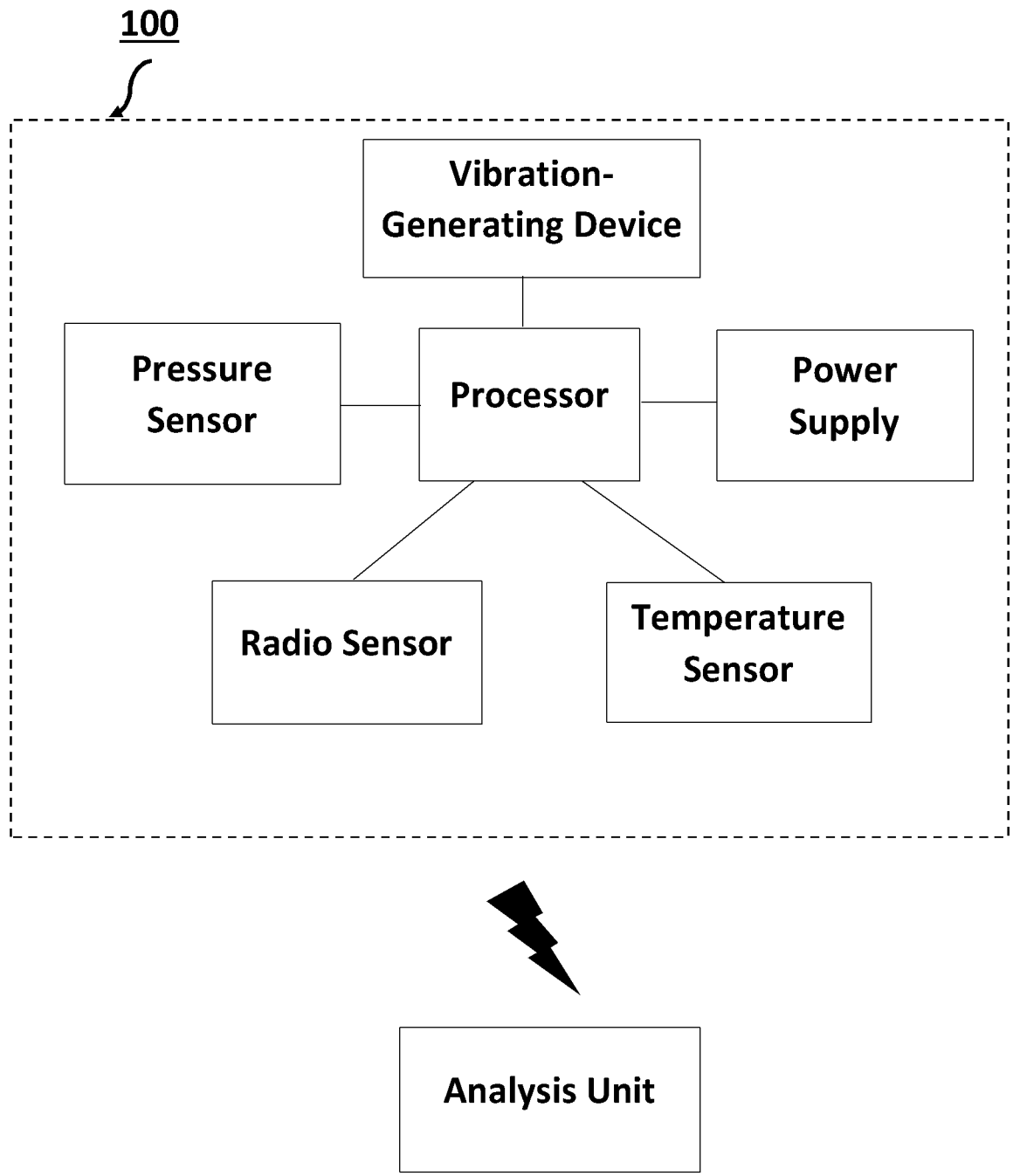

The teat is further characterised in that the vibration-generating device is accommodated in the mouthpiece. When the infant, or the toddler, receives the teat in their mouth and applies some pressure to the mouthpiece, either through their gums and/or through the sucking reflex, the vibration-generating device is activated. Furthermore, in another preferred embodiment of the invention, a pressure sensor is located in the mouthpiece, which may switch on the device as soon as pressure is applied to the mouthpiece, and which may, optionally, switch it off with a short delay time of a few seconds as soon as the pressure disappears.

The pacifier 100 as a whole, particularly, the mouthpiece, preferably consists of silicone, latex, or another moisture-resistant and plasticiser-free synthetic material. Further, the dummies may have a round cherry shape or an orthodontic shape which is flattened at the front and is thus adapted to the shape of the palate in the oral cavity.

Vibration Device

For example, the vibrations may be generated by a small motor which carries an imbalance. Due to its inertia, said imbalance may cause the mouthpiece of the teat to vibrate. Alternatively, it is possible to employ a capsule having a membrane which is subjected to mechanical vibration. It represents the counterweight of the housing which is subjected to vibration by the inertia of the membrane. Corresponding devices may be operated, for example, by miniaturised lithium button cells.

The vibration device may also be equipped with a radio sensor which is in contact with an analysis unit, for example, a smartphone. In this way, the sensor may signal whether the pacifier has been activated or not. Moreover, other information may in principle be transmitted as well, for example, the body temperature, using a corresponding temperature sensor. Conversely, it is possible to control the mode of the vibration device using an analysis unit and a corresponding app, particularly, the vibration frequency which, for example, may be adjusted from 10 to 100 Hertz in a continuously variable manner. In doing so, it is also possible to adjust and to start stored vibration programmes, for example, an increasing or decreasing course of the vibration frequency over time.

INDUSTRIAL APPLICABILITY

Additionally disclosed are the use of the teat of the invention for soothing infants and toddlers as well as the use of a vibration massage of teeth and gums for soothing infants and toddlers.

The invention claimed is:

1. A pacifier, comprising a mouthpiece and a shield, further including a vibration-generating device adapted to generate vibrations in the range of 10 to 100 hertz, wherein the vibration-generating device is accommodated in the mouthpiece, and wherein the vibrations are generated by a motor that carries an imbalance, or comprises a capsule having a membrane, which is subjected to mechanical vibration; and further including a pressure sensor adapted to switch on the device when a selected pressure is applied to the mouthpiece and to switch off the device after a short delay time as soon as the pressure applied to the mouthpiece disappears.

2. The pacifier of claim 1, wherein the outer portion thereof consists of silicone, latex, or another moisture-resistant and plasticiser-free synthetic material.

3. The pacifier of claim 2 further including a radio sensor which is adapted to be in radio contact with an analysis unit.

4. The pacifier of claim 1 having a round cherry shape or an orthodontic shape which is flattened at the front and is thus adapted to the shape of the palate in the oral cavity.

5. The pacifier of claim 1 supplied with power by a miniaturised lithium button cell.

6. The pacifier of claim 1 further including a radio sensor which is adapted to be in radio contact with an analysis unit.

7. The pacifier of claim 6 including at least one temperature sensor adapted to transmit sensed temperature information to the analysis unit.

8. The pacifier of claim 6, wherein the analysis unit represents a smartphone, and that the transmission of information is performed via an app.

9. The pacifier of claim 6 having a round cherry shape or an orthodontic shape which is flattened at the front and is thus adapted to the shape of the palate in the oral cavity.

10. The pacifier of claim 9 supplied with power by a miniaturised lithium button cell.

11. The pacifier of claim 10 including at least one temperature sensor adapted to transmit sensed temperature information to the analysis unit.

12. The pacifier of claim 11, wherein the analysis unit represents a smartphone, and that the transmission of information is performed via an app.

* * * * *